US005700936A

United States Patent [19]

Arzeno

[11] Patent Number: 5,700,936
[45] Date of Patent: Dec. 23, 1997

[54] PROCESS FOR PREPARING A 2-(2-AMINO-1, 6-DIHYDRO-6-OXO-PURIN-9-YL) METHOXY-1,3-PROPANEDIOL VALINATE

[75] Inventor: Humberto B. Arzeno, Cupertino, Calif.

[73] Assignee: Syntex (U.S.A.) Inc., Palo Alto, Calif.

[21] Appl. No.: 592,080

[22] Filed: Jan. 26, 1996

[51] Int. Cl.⁶ .................. C07D 473/18; C07B 43/06
[52] U.S. Cl. ............................................ 544/276
[58] Field of Search ..................................... 544/276

[56] References Cited

U.S. PATENT DOCUMENTS

| | | | |
|---|---|---|---|
| 4,355,032 | 10/1982 | Verheyden et al. | 424/253 |
| 5,043,339 | 8/1991 | Beauchamp | 514/274 |

FOREIGN PATENT DOCUMENTS

| | | |
|---|---|---|
| 0 158 847 | 10/1985 | European Pat. Off. . |
| 0 308 065 | 3/1989 | European Pat. Off. . |
| 0 375 329 | 6/1990 | European Pat. Off. . |
| 1 523 865 | 6/1978 | United Kingdom . |
| 2 104 070 | 3/1983 | United Kingdom . |
| 2 122 618 | 1/1984 | United Kingdom . |
| 8829571 | 6/1990 | United Kingdom . |
| WO 94/29311 | 12/1994 | WIPO . |

OTHER PUBLICATIONS

E. Jensen et al., *Acta Pharm. Nord.* 3(4) 243–247 (1991).
John C. Martin et al., *J. Pharm. Sci.* 76(2), pp. 180–184 (1987).
P.C. Maudgal et al., *Arch. Ophthalmol.* 1984; 102: 140–142.
Leon Colla et al., *J. Med. Chem.* 98, 3, 26, 602–604 (1983).
L. M. Beauchamp et al., *Antiviral Chemistry & Chemotherapy* (1992), 3 (3), 157–164.

*Primary Examiner*—Mark L. Berch
*Attorney, Agent, or Firm*—Heller Ehrman White & McAuliffe

[57] ABSTRACT

Process for preparing the L-monovaline ester of 2-(2-amino-1,6-dihydro-6-oxo-purin-9-yl)methoxy-1,3-propanediol and its pharmaceutically acceptable salts. The present process relates to an improved process whereby ganciclovir is esterified with an L-valine derivative to provide a di-valine ganciclovir intermediate. Removal of one of the valine groups with a lower alkyl amine, benzylamine or benzyl methylamine provides the mono-valine ester compound of Formula I. These products are of value as antiviral agents with improved absorption.

10 Claims, No Drawings

5,700,936

PROCESS FOR PREPARING A 2-(2-AMINO-1, 6-DIHYDRO-6-OXO-PURIN-9-YL) METHOXY-1,3-PROPANEDIOL VALINATE

BACKGROUND OF THE INVENTION

1. Field of the Invention

The present invention relates to a process for preparing a prodrug formulation of ganciclovir and its pharmaceutically acceptable salts. More specifically, the invention relates to a process for preparing the L-monovaline ester derived from 2-(2-amino-1,6-dihydro-6-oxo-purin-9-yl)methoxy-1,3-propane-diol and its pharmaceutically acceptable salts.

2. Background Information

British Patent 1523865 describes antiviral purine derivatives with an acyclic chain in the 9-position. Among those derivatives 2-(2-amino-1,6-dihydro-6-oxo-1,6-dihydro-purin-9-yl)methoxy-ethanol with the INN name acyclovir has been found to have good activity against herpes viruses such as herpes simplex.

U.S. Pat. No. 4,355,032 discloses the compound 9-[(2-hydroxy-1-hydroxymethyl-ethoxy)methyl]-guanine or 2-(2-amino-1,6-dihydro-6-oxo-purin-9-yl)methoxy-1,3-propanediol with the INN name ganciclovir. Ganciclovir is highly efficacious against viruses of the herpes family, for example, against herpes simplex and cytomegalovirus.

European Patent Application EP 0 375 329 discloses prodrug compounds with the following formula

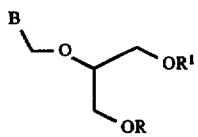

wherein R and $R^1$ are independently selected from a hydrogen atom and an amino acyl residue providing at least one of R and $R^1$ represents an amino acid acyl residue and B represents a group of the formulae

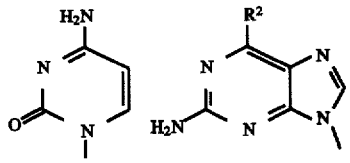

in which $R^2$ represents a $C_{1-6}$ straight chain, $C_{3-6}$ branched chain or $C_{3-6}$ cyclic alkoxy group, or a hydroxy or amino group or a hydrogen atom and the physiologically acceptable salts thereof. These prodrug compounds are described as having advantageous bioavailability when administered the oral route, resulting in high levels of the parent compound in the body.

Example 3 (b) European Patent Application EP 0 375 329 discloses the preparation of the bis(L-isoleucinate) ester of ganciclovir as a white foam. Example 4 (b) discloses the preparation of the bis(glycinate) ester of ganciclovir as a white solid. Example 5 (b) discloses the preparation of the bis (L-valinate) ester of ganciclovir as a solid. Example 6 (b) discloses the preparation of the bis(L-alaninate) ester of ganciclovir as a syrup containing 90% of the bis ester and 10% of the monoester. The bis-esters are prepared by reacting ganciclovir with an optionally protected amino acid or functional equivalent thereof; the reaction may be carried out in a conventional manner, for example in a solvent such as pyridine, dimethylformamide, etc., in the presence of a coupling agent such as 1,3-dicyclohexylcarbodiimide, optionally in the presence of a catalytic base such as 4-dimethylaminopyridine. The described bis esters are non-crystalline materials which are difficult to process for the manufacture of oral pharmaceutical dosage forms.

British Patent Application No. 8829571 is the priority patent application for European Patent Application EP 0 375 329 and U.S. Pat. No. 5,043,339, and discloses amino acid esters of the compounds of the formula

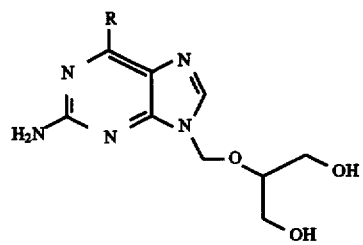

(wherein R represents a hydroxy or amino group or a hydrogen atom) and the physiologically acceptable salts thereof. Examples of preferred amino acids include aliphatic acids e.g. containing up to 6 carbon atoms such as glycine, alanine, valine and isoleucine. The amino acid esters include both mono and diesters. The preparation of the diesters is identical to the preparation in European Patent Application EP 0 375 329; however, this patent application as well as European Patent Application EP 0 375 329 and U.S. Pat. No. 5,043,339 do not disclose the preparation of monoesters, or any data suggesting their usefulness.

Leon Colla et. al., J. Med. Chem. (1983) 26, 602–604 disclose several water-soluble ester derivatives of acyclovir and their salts as prodrugs of acyclovir. The authors indicate that acyclovir cannot be given as eye drops or intramuscular injections because of its limited solubility in water and have therefore synthesized derivatives of acyclovir which are more water soluble than the parent compound. The authors disclose the hydrochloride salt of the glycyl ester, the hydrochloride salt of the alanyl ester, the hydrochloride salt of the β-alanyl ester, the sodium salt of the succinyl ester, and the azidoacetate ester. The alanyl esters were prepared by conventional esterification methods, including reacting acyclovir with the corresponding N-carboxy-protected amino acid in pyridine, in the presence of 1,3-dicyclohexylcarbodiimide and a catalytic amount of p-toluenesulfonic acid and subsequently catalytic hydrogenation to give the alpha- and beta-alanyl esters as their hydrochloride salts.

L. M. Beauchamp et. al., Antiviral Chemistry & Chemotherapy (1992), 3 (3), 157–164 disclose eighteen amino acid esters of the antiherpetic drug acyclovir and their effectiveness as prodrugs of acyclovir, evaluated in rats by measuring the urinary recovery of acyclovir. Ten prodrugs produced greater amounts of the parent drug in the urine than acyclovir itself: the glycyl, D,L-alanyl, L/alanyl, L-2-aminobutyrate, D,L-valyl, L-valyl, DL-isoleucyl, L-isoleucyl, L-methionyl, and L-prolyl ester. According to the authors the L-valyl ester of acyclovir was the best prodrug of the esters investigated. These esters were prepared by methods similar to those employed by Colla et. al.

European Patent Publication 308 065 discloses the Valine and isoleucine esters of acyclovir, preferably in the L-form, as showing a large increase in absorption from the gut after oral administration, when compared with other esters and acyclovir. The amino acid esters are prepared by conventional esterification methods, including reacting acyclovir with an N-carboxy-protected amino acid or an acid halide or acid anhydride of the amino acid, in a solvent such as pyridine or dimethylformamide, optionally in the presence of a catalytic base.

PCT Patent Application WO 94/29311 discloses a process for the preparation of amino acid esters of a nucleoside analogue, including acyclovir and ganciclovir. This process comprises reacting a nucleoside analogue having an esterifiable hydroxy group in its linear or cyclic ether moiety, with a 2-oxa-4-aza-cycloalkane-1,3-dione of the formula

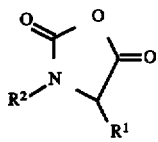

E wherein $R^1$ may represent hydrogen, $C_{1-4}$ alkyl or alkenyl group or other amino acid side chains, and $R^2$ may represent hydrogen or a group $COOR^3$ where $R^3$ is a benzyl, t-butyl, fluorenylmethyl or an optionally halo substituted linear or branched $C_{1-8}$ alkyl group. Preferred $R^1$ groups include hydrogen, methyl, iso-propyl and isobutyl, yielding respectively the glycine, alanine, valine and isoleucine esters of acyclovir or ganciclovir. Examples 1-3 of PCT Patent Application WO 94/29311 discloses only the condensation of acyclovir with the valine-substituted 2-oxa-4-aza-cycloalkane-1,3-dione (Z-valine-N-carboxyanhydride) by conventional procedures. While the amino acid esters of the PCT application include both the acyclovir and ganciclovir (DHPG) esters, the application does not disclose how to prepare the ganciclovir esters, much less the mono-esters of ganciclovir.

The L-monovaline ester derived from 2-(2-amino-1,6-dihydro-6-oxo-purin-9-yl)methoxy-1,3-propane-diol and its pharmaceutically acceptable salts are potent antiviral agents and are described in U.S. patent application Ser. No. 281,893, filed Jul. 28, 1994. These compounds have been found to have improved oral absorption and low toxicity. This patent application also discloses certain processes for preparing these esters, different from those described herein.

The present invention relates to an improved process whereby ganciclovir is esterified with an L-valine derivative to provide a di-valine ganciclovir intermediate. Removal of one of the valine groups with a lower alkyl amine, benzylamine or benzyl methylamine provides the mono-valine ester compound of Formula I.

SUMMARY OF THE INVENTION

In a first aspect, this invention provides a process for preparing the compound of the formula I:

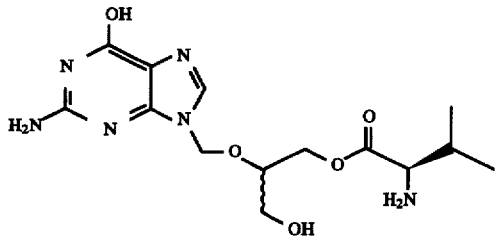

and pharmaceutically acceptable salts thereof, which compound is named hereinafter 2-(2-amino-1,6-dihydro-6-oxo-purin-9-yl)methoxy-3-hydroxy-1-propanyl-L-valinate or mono-L-valine ganciclovir.

This process involves the di-esterification of ganciclovir by an L-valine derivative, followed by removal of one of the valine groups with a lower alkyl amine, benzylamine or benzyl methylamine, and removal of any protecting groups, to yield the prodrug of Formula I. Optionally, the process can also include the formation of salts of the prodrug of Formula I, the conversion of an acid addition salt of the prodrug of Formula I into a non-salt form, the optical resolution of a prodrug of Formula I or the preparation of the prodrugs of Formula I in crystalline form. Details of the process are described below.

DETAILED DESCRIPTION OF THE INVENTION

Definitions

Unless otherwise stated, the following terms used in the specification and claims have the meanings given below:

"Alkyl" means a straight or branched saturated hydrocarbon radical having from one to the number of carbon atoms designated. For example, $C_{1-7}$ alkyl is alkyl having at least one but no more than seven carbon atoms, e.g. methyl, ethyl, i-propyl, n-propyl, n-butyl, n-pentyl, n-heptyl and the like.

"Lower alkyl" means an alkyl of one to six carbon atoms.

"Aryl" means an organic radical derived from an aromatic hydrocarbon by the removal of one hydrogen atom. Preferred aryl radicals have six to twelve carbon atoms as ring carbon atoms in the aromatic hydrocarbon.

"Aralkyl" means an organic radical derived from an aralkane in which an alkyl hydrogen atom is substituted by an above-defined aryl group.

"Acyl" means an organic radical derived from an organic acid by the removal of the hydroxyl group; e.g., $CH_3CO$— is the acyl radical of $CH_3COOH$, or acetyl. Other examples for such acyl groups are propionyl, or benzoyl, etc. The term "acyl" includes the term "alkanoyl" which is the organic radical RCO— in which R is an alkyl group as defined above.

"Lower alkoxy", "(lower alkyl)amino", "di(lower alkyl) amino", "(loweralkanoyl)amino", and similar terms mean alkoxy, alkylamino, dialkylamino, alkanoylamino, etc. in which the or each alkyl radical is a "lower alkyl" as described above.

"Halogen" or "halo" means fluorine, chlorine, bromine, or iodine.

"Lower alkyl amine" means a straight or branched organic radical $R^1N(R^2)_2$ wherein $R^1$ is lower alkyl and $R^2$ is hydrogen or lower alkyl, and lower alkyl is as defined above.

"Derivative" of a compound means a compound obtainable from the original compound by a simple chemical process.

"Activated derivative" of a compound means a reactive form of the original compound which renders the compound active in a desired chemical reaction, in which the original compound is only moderately reactive or non-reactive. Activation is achieved by formation of a derivative or a chemical grouping within the molecule with a higher free energy content than that of the original compound, which renders the activated form more susceptible to react with another reagent. In the context of the present invention activation of the carboxy group is of particular importance and corresponding activating agents or groupings which activate the carboxy group are described in more detail below. An example of an activated derivative of L-valine is She compound of Formula II:

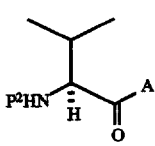

wherein $P^2$ is an amino-protecting group and A is a carboxy-activating group, for example, halo, a lower acyloxy group, a carbodiimide group, such as 1-ethyl-3-(3-dimethylaminopropyl)carbodiimide (EDAC), an isobutyrate group, and the like.

Of particular interest for the present invention is an amino acid anhydride which is an activated form of an amino acid which renders the amino acid (especially L-valine) susceptible to esterification. Amino acid anhydrides are included in the compounds of Formula II, above. Especially useful for the present invention are the cyclic amino acid anhydrides of L-valine, described in PCT Patent Application WO 94/29311, such as 2-oxa-4-aza-5-isopropyl-cycloalkane-1,3-dione of formula IIa:

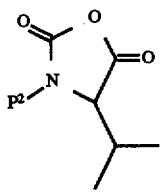

in which $P^2$ is an amino protecting group. Other examples of the cyclic amino acid anhydrides are protected amino acid N-carboxy anhydrides (NCA's) described in more detail below.

"Protecting group" means a chemical group that (a) preserves a reactive group from participating in an undesirable chemical reaction; and (b) can be easily removed after protection of the reactive group is no longer required. For example, the benzyl group is a protecting group for a primary hydroxyl function.

"Amino-protecting group" means a protecting group that preserves a reactive amino group that otherwise would be modified by certain chemical reactions. The definition includes the formyl group or lower alkanoyl groups with 2 to 4 carbon atoms, in particular the acetyl or propionyl group, the trityl or substituted trityl groups, such as the monomethoxytrityl group, dimethoxytrityl groups such as the 4,4'-dimethoxytrityl or 4,4'-dimethoxytriphenylmethyl group, the trifluoroacetyl group, and the N-(9-fluorenylmethoxycarbonyl) or "FMOC" group, the allyloxy-carbonyl group or other protecting groups derived from halocarbonates such as ($C_8$–$C_{12}$)aryl lower alkyl carbonates (such as the N-benzyloxycarbonyl group derived from benzylchlorocarbonate), or derived from biphenylalkyl halo carbonates, or tertiary alkyl halo carbonates, such as tertiary butylhalocarbonates, in particular tertiary butylchlorocarbonate, or di(lower) alkyldicarbonates, in particular di(t-butyl)-dicarbonate, the phthalyl group and the triphenylmethyl halides such as triphenylmethyl chloride, and trifluoroacetic anhydride.

"Leaving group" means a labile group that is replaced in a chemical reaction by another group. Examples of leaving groups are halogen, the optionally substituted benzyloxy group, the isopropyloxy group, the mesyloxy group, the tosyloxy group or the acyloxy group.

All the activating and protecting agents employed in the preparation of the compound of Formula I must meet the following qualifications: (1) their introduction should proceed quantitatively and without racemization of the L-valine component; (2) the protecting group present during the desired reaction should be stable to the reaction conditions to be employed; and (3) the group must be readily removed under conditions in which the ester bond is stable and under which racemization of the L-valine component of the ester does not occur.

The process of the invention may also include the optical resolution of a prodrug of Formula I. Terminology relating to the stereochemistry and optical resolution of these compounds is described in U.S. patent application Ser. No. 281,893, abandoned incorporated herein by reference.

"Optional" or "optionally" means that a described event or circumstance may or may not occur, and that the description includes instances where said event Or circumstance occurs and instances in which it does not. For example, "optionally substituted phenyl" means that the phenyl may or may not be substituted and that the description includes both unsubstituted phenyl and phenyl wherein there is substitution; "optionally followed by converting the free base to the acid addition salt" means that said conversion may or may not be carried out in order for the process described to fall within the invention, and the invention includes those processes wherein the free base is converted to the acid addition salt and those processes in which it is not.

"Pharmaceutically acceptable" means that which is useful in preparing a pharmaceutical composition that is generally safe and non-toxic and includes that which is acceptable for veterinary use as well as human pharmaceutical use.

"Pharmaceutically acceptable salts" means salts which possess the desired pharmacological activity and which are neither biologically nor otherwise undesirable. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentane-propionic acid, glycolic acid, pyruvic acid, lactic acid, malonic acid, succinic acid, malic acid, maleic acid, fumaric acid, tartaric acid, citric acid, benzoic acid, o-(4-hydroxy-benzoyl)-benzoic acid, cinnamic acid, mandelic acid, methanesulfonic acid, ethanesulfonic acid, 1,2-ethane-disulfonic acid, 2-hydroxyethane-sulfonic acid, benzenesulfonic acid, p-chlorobenzenesulfonic acid, 2-naphthalenesulfonic acid, p-toluenesulfonic acid, camphorsulfonic acid, 4-methyl-bicyclo[2.2.2]oct-2-ene-1-carboxylic acid, gluco-heptonic acid, 4,4'-methylenebis(3-hydroxy-2-naphthoic) acid, 3-phenylpropionic acid, trimethyl-acetic acid, tertiary butylacetic acid, lauryl sulfuric acid, gluconic acid, glutamic acid, hydroxy-naphthoic acids, salicylic acid, stearic acid, muconic acid, and the like. Preferred pharmaceutically acceptable salts are those formed with hydrochloric, sulfuric, phosphoric acid, acetic or methanesulfonic acid, ethanesulfonic acid, 1,2-ethanedisulfonic acid, 2-hydroxyethanesulfonic acid, benzene-sulfonic acid, p-chlorobenzenesulfonic acid, and 2-naphthalenesulfonic acid, p-toluenesulfonic acid, camphorsulfonic acid.

Synthetic Reaction Parameters

Unless specified to the contrary, the reactions described herein take place at atmospheric pressure within a temperature range from 5° C. to 170° C. (preferably from 10° C. to 50° C.; most preferably at "room" or "ambient" temperature, e.g., 20°–30° C.). However, there are clearly some reactions where the temperature range used in the chemical reaction will be above or below these temperature ranges. Further, unless otherwise specified, the reaction times and conditions are intended to be approximate, e.g., taking place at about atmospheric pressure within a temperature range of about 5° C. to about 100° C. (preferably from about 10° C. to about 50° C.; most preferably about 20° C.) over a period of about 1 to about 100 hours (preferably about 5 to 60 hours). Parameters given in the Examples are intended to be specific, not approximate.

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can, of course, also be used.

Presently Preferred Embodiments

While the broadest definition of this invention is set forth in the Summary of the Invention as a process for preparing the compound of Formula I and its pharmaceutically acceptable salts, the (R,S) mixture and certain salts are preferred.

The following acids are preferred to form pharmaceutically acceptable salts with the compound of Formula I: hydrochloric, sulfuric, phosphoric acid, acetic, methanesulfonic, ethanesulfonic, 1,2-ethanedisulfonic, 2-hydroxyethanesulfonic, benzenesulfonic, p-chlorobenzenesulfonic, 2-naphthalenesulfonic, p-toluenesulfonic and camphorsulfonic acid. Most preferred are strong inorganic acids, such as hydrochloric, sulfuric or phosphoric acid.

The most preferred compounds are 2-(2-amino-1,6-dihydro-6-oxo-purin-9-yl)methoxy-3-hydroxy-1-propanyl L-valinate hydrochloride and acetate. These compounds can be prepared as crystalline materials and therefore can be easily manufactured into stable oral formulations.

In any of the processes described herein, a reference to Formula I, II, III or IV refers to such Formulae wherein $P^1$, $P^2$, and A are as defined in their broadest definitions set forth in the Summary of the Invention, with the processes applying particularly to the presently preferred embodiments.

Details of the Synthetic Processes

The process of the present invention is depicted in the Reaction Sequence shown below:

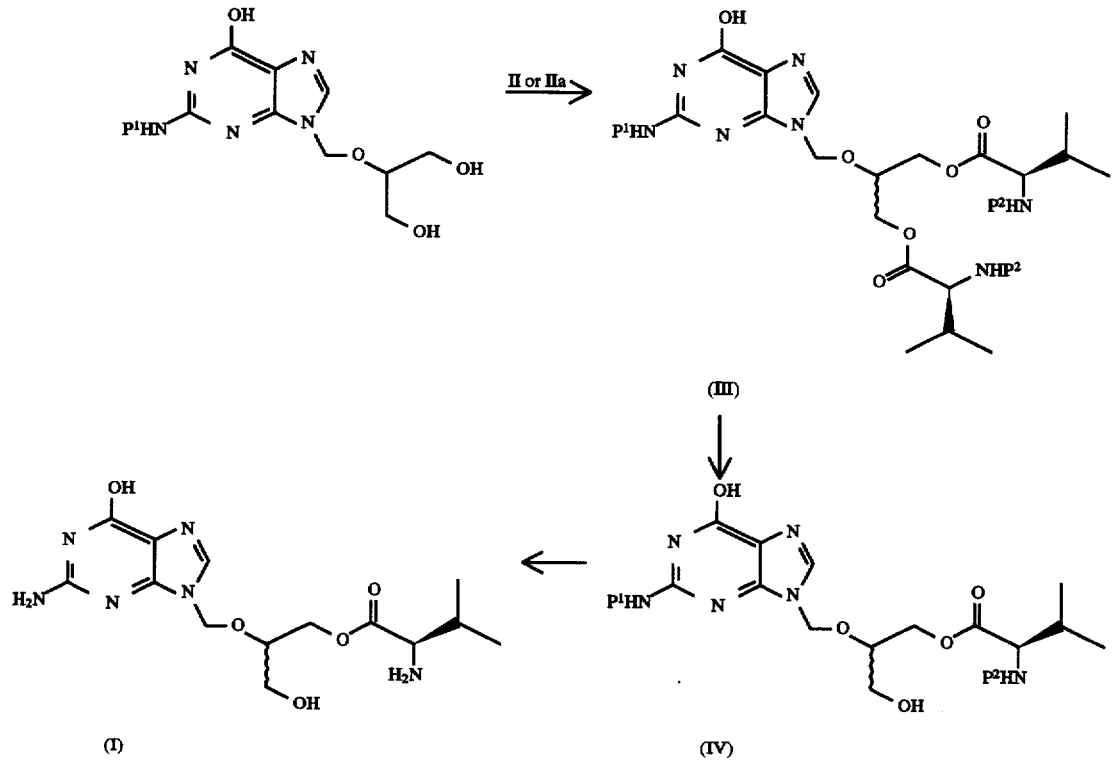

wherein $P^1$ is hydrogen or an amino protecting group, and $P^2$ is an amino protecting group.

2-(2-amino-1,6-dihydro-6-oxo-purin-9-yl)methoxy-1,3-propanediol (ganciclovir) is esterified with an L-valine derivative of Formula II or IIa to form a di-valine ester of ganciclovir (Formula III). Removal of one of the valine groups with a lower alkyl amine, benzylamine or benzyl methylamine, followed by removal of any protecting groups, affords the compound of Formula I.

Compounds of Formula I can optionally be converted into a pharmaceutically acceptable salt thereof. The process can also include the conversion of an acid addition salt of the prodrug of Formula I into a non-salt form, the optical resolution of a compound of Formula I or the preparation of the compound of Formula I in crystalline form.

The process for producing the compound of Formula I may or may not involve protection of the amino group in the 2-position of the guanine base (see the detailed description below of Steps I through III for the case in which the process is carried out without a protected amino group). For the case when the ganciclovir starting material does have a protected 2-amino group, the protecting group may be removed by conventional procedures, well-known in the art. For example, if the amino-protecting group is a lower alkanoyl group basic conditions (pH between 8 to 11) are employed to remove the protecting group. For example, 2-N-acetyl-ganciclovir is treated with an alkaline reagent such as ammonium hydroxide, sodium or potassium carbonate or sodium or potassium hydroxide until the removal of the acetyl group is complete. In general, this reaction will be conducted in the presence of a suitable solvent such as a lower alkanol. Preferably the starting material is dissolved in methanol and a stoichiometric excess of ammonium hydroxide is added. The reaction temperature is kept between 0° to 50° C., preferably at room temperature. After the reaction is complete (which can be determined by TLC), another solvent may be added to facilitate isolation of the de-protected product, such as ethyl ether which leads to precipitation of the de-acylated product which can be filtered off and isolated using conventional separation methods.

Starting Materials

All starting materials employed to make the compound of Formula I are known, such as ganciclovir, and the protecting and carboxylic-group-activating reagents.

Prior to carrying out Step II (esterification step), the amino group of the L-valine derivative must be protected to avoid its interference with the esterification by undesirable amide formation. The various amino-protected L-valine derivatives useful in this invention, such as N-benzyloxycarbonyl-L-valine, BOC-L-valine and FMOC-L-valine, N-formyl-L-valine and N-benzyloxycarbonyl-N-carboxy-L-valine anhydride, are all commercially available (SNPE Inc., Princeton, N.J., Aldrich Chemical Co., Milwaukee, Wis. and Sigma Chemical Co., St. Louis, Mo.), or are described in the literature, such as N-allyloxycarbonyl-L-valine. Cyclic amino-protected L-valine derivatives are also described in the literature, as noted above. Of particular interest for the present invention is the benzyloxycarbonyl valine-substituted 2-oxa-4-aza-cycloalkane-1,3-dione (Z-valine-N-carboxyanhydride, or Z-Valine-NCA), which is also commercially available (SNPE Inc., Princeton, N.J.). Alternatively, the protecting step may be carried out by conventional methods.

A preferred ganciclovir starting material for the preparation of the compound of the invention is the unprotected ganciclovir (2-(2-amino-1,6-dihydro-6-oxo-purin-9-yl) methoxy-1,3-propanediol) which is described in U.S. Pat. No. 4,355,032. Other ganciclovir starting materials may have protection at the 2-amino group, such as 2-(2-acyl-amino-1,6-dihydro-6-oxo-purin-9-yl)methoxy-1,3-propandiol.

Preparation of Activated Derivative of L-valine

Prior to carrying out Step I (esterification step), L-valine must also be activated. At least 1 equivalent of the protected amino acid and 1 equivalent of a suitable coupling agent or dehydrating agent, for example 1,3-dicyclohexylcarbodiimide or salts of such diimides with basic groups should be employed from the start. Other carbodiimides such as N,N'-carbonyldiimidazole may also be used. Further useful dehydrating agents are trifluoroacetic anhydride, mixed anhydrides, acid chlorides, 1-benzo-triazolyloxy-tris(dimethylamino)phosphonium hexafluorophosphate, benzotriazole-1-yl-oxy-trispyrrolidinophosphoniumhexafluorophosphate, 1-hydroxybenzotriazole, 1-hydroxy-4-azabenzotriazole, 1-hydroxy-7-azabenzotriazole, N-ethyl-N"-(3-(dimethylamino)-propyl)carbodiimide hydrochloride, 3-hydroxy-3,4-dihydro-4-oxo-1,2,3-benzotriazine, O-(benzotriazol-1-yl)-1,1,3,3-tetramethyluroniumhexafluorophosphate, O-(7-azabenzotriazol-1-yl)-1,1,3,3-tetramethyluronium hexafluorophosphate, O-(7-azabenzotriaborate, O-(1H-benzotriazol-1-yl)-1,1,3,3-bis(tetramethylene)uronium hexafluorophosphate or O-(7-azabenzotriazol-1-yl)-1,1,3,3-bis(tetramethylene)uronium hexafluorophosphate. A description of these coupling agents by L. A. Carpino can be found in J. Am. Chem. Soc. 1993, 115, p. 4397–4398.

Also useful for this purpose are urethane-protected amino acid N-carboxy anhydrides (UNCA's) which are an activated form of an amino acid; these have been described by William D. Fuller et al., J. Am. Chem. Soc. 1990, 112, 7414–7416, which is incorporated herein by reference. Other protected amino acid N-carboxy anhydrides are described in PCT Patent Application WO 94/29311 discussed above. In summary, any other reagent that produces an anhydride or another activated derivative of the protected amino acid under mild conditions can be used as the coupling agent.

The amino-protected amino acid is dissolved in an inert solvent such as a halogenated lower alkane, preferably dichloromethane under an inert atmosphere, for example nitrogen, and the coupling agent is added (preferably 1,3-dicyclohexylcarbodiimide). The reaction mixture is stirred at temperatures between 0° and 50° C. preferably at about room temperature. The reaction mixture is filtered and the reaction product (the anhydride of the protected amino acid) isolated. The resulting product is dissolved in a dry inert solvent such as dry dimethylformamide and placed under nitrogen.

Preparation of Mono-L-valine Ganciclovir

Step I:

Ganciclovir with an optionally protected 2-amino group is esterified with an L-valine derivative of Formula II to give the di-valine ester of ganciclovir as an intermediate (Formula III). Suitable amino-protecting groups are lower alkanoyl groups with 2 to 4 carbon atoms, in particular the acetyl or propionyl group. Other suitable amino-protecting groups are the trityl or substituted trityl groups, such as the monomethoxytrityl group, and the 4,4'-dimethoxytrityl group.

Suitable amino-protecting groups for the L-valine derivative are the N-benzyloxycarbonyl group, the phthalyl group, the tertiary butyloxycarbonyl group and the N-(9-fluorenylmethoxycarbonyl) or "FMOC" group.

The di-valine ester of ganciclovir can be prepared by conventional procedures, such as those described in European Patent 0 375 329.

Another example of a conventional procedure for preparing the di-valine ester is as follows. A suspension of ganciclovir is reacted with a solution containing approximately equivalent amount of the L-valine derivative, preferably $N^\alpha$-Boc-Valine-NCA, and an organic base, such as triethylamine (TEA) at 10°–50° C. preferably at ambient temperature for 10–90 hours, preferably about 24 hours. The reaction mixture is diluted, filtered, washed and dried under vacuum.

Step II:

The conversion of the di-valine ester of ganciclovir to the mono-(L-valinate)-ganciclovir is effected by partial hydrolysis of one of the L-valine ester moieties with a lower alkyl amine, benzylamine or benzyl methylamine, preferably with n-propylamine in a nonpolar aprotic solvent such as hexane. This results in cleavage of one of the amino acyl residues.

For example the di-valine ester of ganciclovir is treated with n-propylamine in a nonpolar aprotic solvent, preferably hexane, and stirred at 10°–50° C., preferably at ambient temperature, for 1 hour to 10 days, preferably from 1 to 7 days. The reaction mixture is evaporated under vacuum and analyzed by HPLC.

Step III (Final De-protection to Give the Product of Formula I):

The valine protecting group of the product of Step II is removed by a de-protection reaction, preferably in an acidic medium or solvent, most preferably by hydrogenolysis. De-protection under acidic conditions is preferred, as this will ensure that the amino group liberated in the de-protection reaction will be protonated; that is, that the base of Formula I as it is formed in the de-protection reaction will be captured by an at least stoichiometric amount of acid present. Isolating the compound of Formula I as an acid addition salt will protect the desired stereoconfiguration of the compound of Formula I. Therefore, those examples given below that show the de-protection step also show the concomitant salt formation step.

The de-protection reaction is carried by dissolving the product of the previous step in an inert solvent, preferably in an acidic solvent, using a hydrogenation catalyst, such as platinum, or palladium hydroxide on carbon or palladium on carbon, using elevated hydrogen pressure between 1 and 2000 psi, preferably 50 to 200 psi, most preferably 5 to 20 psi. The completion of the reaction can be monitored using conventional TLC analysis. The hydrogenolysis is continued until the conversion is complete, if required with addition of further hydrogenation catalyst. The catalyst is removed and washed. The combined filtrates from filtration and the washings are concentrated and lyophilized to isolate ganciclovir L-valine ester. The purification of the product and the isolation of a crystalline ester is carried out by recrystallization or other purification techniques, such as liquid chromatographic techniques.

If present, any protecting group at the 2-amino group of the guanine group may be removed by conventional procedures, as described above.

If the tertiary butyloxycarbonyl group is being used as amino-protecting group, its removal is effected with acid, such as HCl and isopropanol as a solvent or with trifluoroacetic acid neat.

Alternatively if the esterification step has been carried out with a trityl or substituted trityl-protected ganciclovir derivative such protecting groups can be removed by treatment with an aqueous alkanoic acid or trifluoroacetic or hydrochloric acid at temperatures between −20° C. and 100° C., for example, aqueous acetic acid.

Preparation of Salts

One of ordinary skill in the art will also recognize that the compound of Formula I may be prepared as an acid addition salt or as the corresponding free base. If prepared as an acid addition salt, the compound can be converted to the free base by treatment with a suitable base such as ammonium hydroxide solution, sodium hydroxide, potassium hydroxide or the like. However, it is important to point out that the free base of Formula I is more difficult to characterize than its acid addition salts. When converting the free base to an acid addition salt, the compound is reacted with a suitable organic or inorganic acid (described earlier). These reactions are effected by treatment with an at least stoichiometric amount of an appropriate acid (in case of the preparation of an acid addition salt) or base (in case of liberation of the free compound of Formula I). In the salt-forming step of this invention, typically the free base is dissolved in a polar solvent such as water or a lower alkanol (preferably isopropanol) and mixtures thereof and the acid is added in the required amount in water or in lower alkanol. The reaction temperature is usually kept at about 0° to 50° C., preferably at about room temperature. The corresponding salt precipitates spontaneously or can be brought out of the solution by the addition of a less polar solvent, removal of the solvent by evaporation or in a vacuum, or by cooling the solution.

Isolation of Stereoisomers and the Manufacture of Crystalline 2-(2-Amino-1,6-dihydro-6-oxo-purin-9-yl)methoxy-3-hydroxy-1-propanyl-L-valinate From the Formula (I) it is apparent that the compound of the invention has one asymmetric carbon atom (chiral center) in the propanyl chain, in addition to the asymmetric carbon atom in L-valine. Therefore, two diastereomeric forms exist, the (R)- and (S)- form as determined by the rules of Cahn et al. Suitable methods for the separation of the diastereomers are described in U.S. patent application Ser. No. 281,893, incorporated herein by reference.

The compounds of Formula (I) may also be prepared in crystalline form, which has many well-known advantages over the non-crystalline form. Suitable methods for the preparation of the compounds of the invention in crystalline form are also described in U.S. patent application Ser. No. 281,893, incorporated herein by reference.

The following preparations and examples are given to enable those skilled in the art to more clearly understand and to practice the present invention. They should not be considered as limiting the scope of the invention, but merely as being illustrative and representative thereof.

EXAMPLE 1

Preparation of 2-(2-Amino-1,6-dihydro-6-oxo-purin-9-yl)methoxy-1,3-propanediyl-bis[N-(butyloxycarbonyl)-L-valinate] and 2-(2-Amino-1,6-dihydro-6-oxo-purin-9-yl)methoxy-1,3-propanediyl-bis[N-(benzyloxycarbonyl)-L-valinate]

1A. Preparation of O,O,bis $N^\alpha$-Boc-Valine-ganciclovir

To a suspension of ganciclovir (4 gm) in dimethylformamide (25 ml) was added triethylamine (2.32 ml) and $N^\alpha$-Boc-Valine-NCA (11 gm) and stirred at room temperature overnight. The reaction mixture was diluted with water, filtered, washed with water and dried overnight. The solid was dissolved in ethyl acetate and washed with a sodium bicarbonate solution (5%), washed with water, dried over sodium sulfate, filtered and evaporated. The residue was dissolved in acetone and precipitated by addition over petroleum ether and the solid filtered and dried under vacuum overnight to give 10 gm of the product.

1B. Preparation of O,O,bis $N^\alpha$-Z-Valine-ganciclovir

To a suspension of ganciclovir (5 gm) in dimethylformamide (30 ml) was added triethylamine (2.5 ml) and the N$^\alpha$-Z-Valine-NCA (7.5 gm), and half hour later another portion (7.5 gm). After 3 hours from the initial addition, water was added and the reaction mixture was extracted with ethyl acetate. The organic phase was washed successively with sodium bisulfate solution (5%), water, sodium bicarbonate solution (5%), water, and brine, and then dried over sodium sulfate, filtered and evaporated. The residue was dissolved in toluene and precipitated by hexane addition. The solid was filtered washed with hexane, and dried under vacuum to give 15 gm of product.

EXAMPLE 2

Preparation of 2-(2-Amino-1,6-dihydro-6-oxo-purin-9-yl) methoxy-3-hydroxy-1-propanyl-N-(butyloxycarbonyl)-L-valinate and 2-(2-Amino-1,6-dihydro-6-oxo-purin-9-yl) methoxy-3-hydroxy-1-propanyl-N-(benzyloxycarbonyl)-L-valinate 2A. Preparation of O-(N$^\alpha$-Boc-Valine)-ganciclovir O,O,bis N$^\alpha$-Boc-Valine ganciclovir (50 mg) in hexane (10 ml) and n-propylamine (1 ml) was stirred at room temperature for 7 days. The reaction mixture was evaporated under vacuum and the product analyzed by HPLC as a mixture of 11% ganciclovir, 74% mono-valine ganciclovir, and 15% bis-valine ganciclovir.

2B. Preparation of O-(N$^\alpha$-Z-Valine)-ganciclovir

O,O,bis N$^\alpha$-Z-Valine ganciclovir(2 gm) in n-propylamine (10 ml) and hexanes (20 ml) was stirred at room temperature; after 7 hours, 5 ml of hexanes were added and the reaction mixture stirred for another 24 hours, evaporated. HPLC showed a mixture of 31% ganciclovir, 57.5% mono-valine ganciclovir and 11.5% bis-valine ganciclovir.

EXAMPLE 3

Preparation of 2-(2-Amino-1,6-dihydro-6-oxo-purin-9-yl) methoxy-3-hydroxy-1-propanyl-L-valinate A vigorously stirred suspension of Pd(OH)$_2$/C (670 g) in CH$_3$OH (23 L) was treated with H$_2$ gas (7 psi) for 12 hours. To this suspension was added a solution O-(N$^\alpha$-Z-Valine)-ganciclovir (6.7 kg, 13.7 moles) in CH$_3$OH (34 L) containing concentrated HCl (1.64 kg). The H$_2$ atmosphere was maintained at 7 psi, and replaced at 20 minute intervals. After 2.75 hours, the H$_2$ atmosphere was replaced with nitrogen. The catalyst was removed by filtration through Solka Floc. The filtrate was concentrated in vacuo to approximately 13 L, at which time H$_2$O (4 L) was added. The volume of the filtrate was again reduced to approximately 13 L. The temperature of the mixture was adjusted to approximately 38° C. and isopropyl alcohol (24 L) was slowly added. After crystallization had occurred, the mixture was cooled to 21° C. over a period of 2 hours. Additional isopropyl alcohol (24 L) was added and the mixture was stirred for 16 hours at 5° C. The solid was then collected by filtration. The filtercake was washed with cold isopropyl alcohol (19 L) and dried under a stream of nitrogen for 3 days. The solid was placed in a vacuum oven (55° C., nitrogen bleed, 25 ins vacuum). Isopropyl alcohol was found to be 0.4% after 24 hours. Weight of solid: 4.35 kg. Purity: (HPLC) 98.6%: MS: 355 (MH)$^+$.

What is claimed is:

1. A process for preparing the compound 2-(2-amino-1,6-dihydro-6-oxo-purin-9-yl) methoxy-3-hydroxy-1-propanyl-L-valinate or a pharmaceutically acceptable salt or diastereomer thereof, comprising:

(a) hydrolyzing a compound of formula III

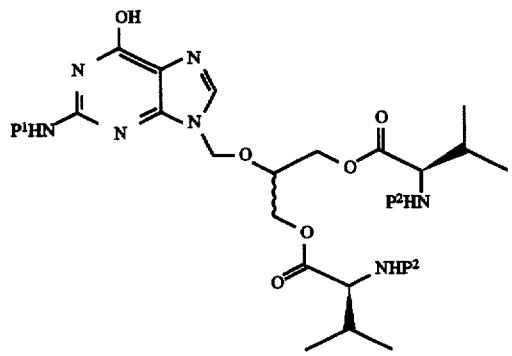

wherein P$^1$ is hydrogen or an amino-protecting group, and P$^2$ is an amino-protecting group, to a compound of formula IV

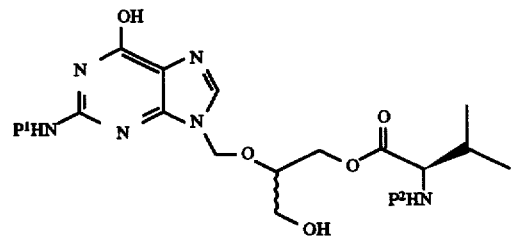

wherein P$^1$ and P$^2$ are as defined above, in the presence of an amine selected from a lower alkyl amine, benzylamine or benzyl methylamine, in a nonpolar aprotic solvent; and (b) deprotecting the compound of formula IV to 2-(2-amino-1,6-dihydro-6-oxo-purin-9-yl)methoxy-3-hydroxy-1-propanyl-L-valinate or a pharmaceutically acceptable salt thereof; optionally followed by (c) converting 2-(2-amino-1,6-dihydro-6-oxo-purin-9-yl) methoxy-3-hydroxy-1-propanyl-L-valinate into a pharmaceutically acceptable salt thereof; or (d) separating the 2-(2-amino-1,6-dihydro-6-oxo-purin-9-yl)methoxy-3-hydroxy-propanyl-L-valinate into its (R) and (S) diastereomers.

2. The process of claim 1 wherein the amine is n-propylamine.

3. The process of claim 1 wherein the nonpolar aprotic solvent is hexane.

4. The process of claim 1 wherein P$^1$ is lower alkanoyl.

5. The process of claim 4 wherein P$^1$ is acetyl or propionyl.

6. The process of claim 4 wherein step (b) includes basic hydrolysis in methanol in the presence of ammoniun hydroxide.

7. The process of claim 1 wherein P$^2$ is benzyloxycarbonyl or t-butyloxycarbonyl.

8. The process of claim 7 wherein P$^2$ is benzyloxycarbonyl and step (b) includes hydrogenolysis.

9. The process of claim 8 wherein the hydrogenolysis is carried out in methanol/hydrochloric acid in the presence of palladium hydroxide on carbon.

10. The process of claim 7 wherein P$^2$ is t-butyloxycarbonyl and step (b) includes acid hydrolysis in hydrochloric acid or trifluoroacetic acid.

* * * * *